United States Patent [19]

Saunders

[11] Patent Number: 4,835,097
[45] Date of Patent: May 30, 1989

[54] METHOD FOR ASCERTAINING THE HISTORY OF A CONDITION OF THE BODY FROM A SINGLE BLOOD SAMPLE

[76] Inventor: Alexander M. Saunders, 8 Trillium La., San Carlos, Calif. 94020

[21] Appl. No.: 918,934

[22] Filed: Oct. 15, 1986

[51] Int. Cl.$^4$ .......................... C12Q 1/00; C12Q 1/54
[52] U.S. Cl. ........................................ 435/4; 435/2; 435/6; 435/14; 435/15; 424/11; 436/63; 436/67; 436/70; 436/72; 436/94; 436/174; 436/501; 436/520; 436/827; 436/811
[58] Field of Search ...................... 435/2, 4, 6, 14, 15; 436/501, 520, 63, 67, 70, 72, 94, 174, 811, 827; 424/11

[56] References Cited

PUBLICATIONS

Bartosz, G., Biochemical Medicine, 27:398–400 (1982).
Elseweidy M. M. et al., Hemoglobin, 8(4): 363–372 (1984).
Rigal, D. et al, La Presse Medicale, 14, No. 9: 521–523 (3–1985).

*Primary Examiner*—Margaret Moskowitz
*Attorney, Agent, or Firm*—Iver P Cooper

[57] ABSTRACT

A historical time series analysis is obtained from a single sample of blood by measurement of hemoglobin and an altered hemoglobin, for example, glycohemoglobin, on a cell-by-cell basis. The results are compared by ratio of glycohemoglobin to hemoglobin on a cell-by-cell basis. Since the alteration of hemoglobin is continuous and irreversible, the ordered set of ratios represents a time-series of the cells, and any deviation from normal will be readily apparent A time-series can also be derived for other constituents, the time-series representing historical data of the other constituents in the person from whom the blood sample was taken.

42 Claims, 5 Drawing Sheets

FIG. 1a.

MODEL OF CUMULATIVE INCREMENT IN TIME

| TIME-<br>V | BASIC<br>MINIMUM | CONST.<br>BIAS | TEMP.<br>INCR. | TIME<br>SUM | CUMUL.<br>SUM |
|---|---|---|---|---|---|
|  |  | 1 | 0 |  |  |
| 1 |  | 1 | 0 | 1 | 1 |
| 2 |  | 1 | 0 | 1 | 2 |
| 3 |  | 1 | 0 | 1 | 3 |
| 4 |  | 1 | 0 | 1 | 4 |
| 5 |  | 1 | 0 | 1 | 5 |
| 6 |  | 1 | 0 | 1 | 6 |
| 7 |  | 1 | 0 | 1 | 7 |
| 8 |  | 1 | 0 | 1 | 8 |
| 9 |  | 1 | 0 | 1 | 9 |
| 10 |  | 1 | 0 | 1 | 10 |
| 11 |  | 1 | 0 | 1 | 11 |
| 12 |  | 1 | 0 | 1 | 12 |

MEAN 6.5.

FIG. 1b.

PATIENT CHEMISTRY HISTORY (WEEKS)

FIG. 2a.

MODEL OF CUMULATIVE IN TIME

| TIME_V | BASIC MINIMUM | CONST. BIAS | TEMP. INCR. | TIME SUM | CUMUL. SUM |
|---|---|---|---|---|---|
|  | 1 | 1 |  |  |  |
| 1 | 1 | 1 |  | 2 | 2 |
| 2 | 1 | 1 |  | 2 | 4 |
| 3 | 1 | 1 |  | 2 | 6 |
| 4 | 1 | 1 |  | 2 | 8 |
| 5 | 1 | 1 |  | 2 | 10 |
| 6 | 1 | 1 |  | 2 | 12 |
| 7 | 1 | 1 |  | 2 | 14 |
| 8 | 1 | 1 |  | 2 | 16 |
| 9 | 1 | 1 |  | 2 | 18 |
| 10 | 1 | 1 |  | 2 | 20 |
| 11 | 1 | 1 |  | 2 | 22 |
| 12 | 1 | 1 |  | 2 | 24 |

MEAN— 13

FIG. 2b.

PATIENT CHEMISTRY (WEEKS)

FIG. 3a.

MODEL OF CUMULATIVE INCREMENT IN TIME

| TIME-V | BASIC MINIMUM | CONST. BIAS | TEMP. INCR. | TIME SUM | CUMUL. SUM | TIME-V |
|---|---|---|---|---|---|---|
| 1 | 1 | 1 | -.8 | 1.2 | 1.2 | 1 |
| 2 | 1 | 1 | -.7 | 1.3 | 2.5 | 2 |
| 3 | 1 | 1 | -.4 | 1.6 | 4.1 | 3 |
| 4 | 1 | 1 |  | 2 | 6.1 | 4 |
| 5 | 1 | 1 |  | 2 | 8.1 | 5 |
| 6 | 1 | 1 |  | 2 | 10.1 | 6 |
| 7 | 1 | 1 |  | 2 | 12.1 | 7 |
| 8 | 1 | 1 |  | 2 | 14.1 | 8 |
| 9 | 1 | 1 |  | 2 | 16.1 | 9 |
| 10 | 1 | 1 |  | 2 | 18.1 | 10 |
| 11 | 1 | 1 |  | 2 | 20.1 | 11 |
| 12 | 1 | 1 |  | 2 | 22.1 | 12 |
|  |  |  |  | MEAN | 11.225 | MEAN % 11.225 |

FIG. 3b.

PATIENT CHEMISTRY HISTORY (WEEKS)

FIG. 4a.

MODEL OF CUMULATIVE INCREMENT IN TIME

| TIME V | BASIC MINIMUM | CONST. BIAS | TEMP. INCR. | TIME SUM | CUMUL. SUM |
|---|---|---|---|---|---|
|  | 1 | 1 |  |  |  |
| 1 | 1 | 1 | −.9 | 1.1 | 1.1 |
| 2 | 1 | 1 | 0 | 2 | 3.1 |
| 3 | 1 | 1 | −1 | 1 | 4.1 |
| 4 | 1 | 1 | −.8 | 1.2 | 5.3 |
| 5 | 1 | 1 | −.7 | 1.3 | 6.6 |
| 6 | 1 | 1 | −.4 | 1.6 | 8.2 |
| 7 | 1 | 1 |  | 2 | 10.2 |
| 8 | 1 | 1 |  | 2 | 12.2 |
| 9 | 1 | 1 |  | 2 | 14.2 |
| 10 | 1 | 1 |  | 2 | 16.2 |
| 11 | 1 | 1 |  | 2 | 18.2 |
| 12 | 1 | 1 |  | 2 | 20.2 |

MEAN —— 9.9667

FIG. 4b.

PATIENT CHEMISTRY HISTORY (WEEKS)

—— DIAGNOSIS ——  DIABETES— 6 WEEKS RX

FIG. 5a.

MODEL OF CUMULATIVE INCREMENT IN TIME

| TIME $\_$ $V$ | BASIC MINIMUM | CONST. BIAS | TEMP. INCR. | TIME SUM | CUMUL. SUM |
|---|---|---|---|---|---|
|   | 1 | 0 |   |   |   |
| 1 | 1 | 0 |   | 1 | 1 |
| 2 | 1 | 0 |   | 1 | 2 |
| 3 | 1 | 0 |   | 1 | 3 |
| 4 | 1 | 0 |   | 1 | 4 |
| 5 | 1 | 0 |   | 1 | 5 |
| 6 | 1 | 0 | 1 | 2 | 7 |
| 7 | 1 | 0 |   | 1 | 8 |
| 8 | 1 | 0 |   | 1 | 9 |
| 9 | 1 | 0 |   | 1 | 10 |
| 10 | 1 | 0 |   | 1 | 11 |
| 11 | 1 | 0 |   | 1 | 12 |
| 12 | 1 | 0 |   | 1 | 13 |

MEAN 7.0833

FIG. 5b.

PATIENT CHEMISTRY HISTORY (WEEKS)

DIAGNOSIS — DIABETIC, ONE PERIOD OUT OF CONTROL

MEAN % 7.0833

METHOD FOR ASCERTAINING THE HISTORY OF A CONDITION OF THE BODY FROM A SINGLE BLOOD SAMPLE

FIELD OF THE INVENTION

The invention relates to a method for detecting and measuring a physical condition recognizable from comparison of blood cells of different ages from a patient.

BACKGROUND OF THE INVENTION

Hitherto, a historical record of a physical condition has not been obtainable unless an indicator of the condition or disorder has been measured concurrently with the progression of the condition or disorder.

Red blood cells contain hemoglobin, a complex molecule involved in the transport of oxygen and carbon dioxide in the blood. They continuously enter into the circulation from the bone marrow, where they are made. The red blood cells first entering the blood stream are termed reticulocytes, and after the "reticulum" of nucleic acid material is eliminated from the reticulocytes, in the first two days of circulation, the red blood cells continue to circulate, as mature cells, for 120 days in normal people. After this time the red blood cells are eliminated from circulation and from the body.

It is well known that during their lifetime, red blood cells are bathed in fluid plasma with a continuously changing chemical composition. Some components of the plasma also move freely into and out of the red blood cell through the cell membrane. While in the red blood cell, some of these components exert an influence on the constituent molecules of the red blood cells, particularly on the hemoglobin molecule.

The hemoglobin (Hb) molecule consists of heme (a pigment) and globin (a protein). The heme contains iron in the ferrous state. The protein moiety is formed by two alpha-chains (141 amino acids) and two beta chains (146 A.A.). Normal hemoglobin is called hemoglobin A (HbA). Over 100 amino acid sequence variants are known.

A variety of chemically modified forms of hemoglobin are known. $O_2$ combines rapidly and reversibly with hemoglobin to form oxyhemoglobin. When the iron of the hemoglobin is oxidized to the ferric form, methemoglobin is formed. This change is reversed by DPNH and methemoglobin reductase. Hb is irreversibly converted to sulfhemoglobin by certain drugs. Carboxyhemoglobin is made when carbon monoxide binds to hemoglobin. Cyanohemoglobin is the reaction product of Hb and cyanide ion.

Glycosylated hemoglobins are known. Ashby, et al., Diabetic Medicine 2:83-87 (1985); Mortensen, Danish Medical Bulletin, 36:369-328 (1985); Howard, et al., Acta Paediatr. Scand. 70:695-698 (1981); Mortensen, J. Chromatogr. 182:325-33 (1980). Glycohemoglobins retain the original function of hemoglobin, the transport of oxygen. The amount of glycohemoglobin formed is directly proportional to the concentration of glucose in circulating plasma which surrounds the red blood cells, and the time of exposure.

The proportion of glycohemoglobin to hemoglobin in a blood sample may be measured, and this measurement is performed as a chemical test, the general concept being the subject of U.S. Pat. Nos. 4,399,227, 4,448,888, 4,438,204, 4,372,747, and 4,465,774. In these tests, the hemoglobin and glycohemoglobin from cells of different ages has been mixed indiscriminately.

The five most prominent glycosylated hemoglobins are collectively designated $HbA_1$. They are $HbA_{1a1}$ (0.2%), $HbA_{1a2}$ (0.2%), $HbA_{1b}$ (0.5%), $HbA_{1c}$ (4-6%) and $HbA_{1d}$ (0.2-0.6%). HbA and $HbA_1$ combined make up about 97% of the total hemoglobin content.

Glycohemoglobin measurements have attracted attention as a possible indicator of dietary compliance by diabetics, see Howard, et al., Acta Pediatr. Scand., 70:695-98 (1981).

Hoberman, U.S. Pat. No. 4,463,098, provides for measuring the average historical record of alcohol consumption in a patient by recording the concentration of a hemoglobin molecule altered by reaction with a modified sugar, 5-deoxy-D-xylulose-1-phosphate (DXP) to form "DXP-hemoglobin". The sugar molecule becomes trapped on the hemoglobin molecule due to the indirect action of alcohol on the normal breakdown mechanism of sugar in the red blood cells. The measurements of the Hoberman patent are not made on a cell-by-cell basis, and they tend to average the day-to-day changes in alcohol level.

It is generally accepted that erythrocytes may be separated according to age on the basis of relative densities. Van Gastel, 1968-RVI, Methods for Studying the In Vivo Aging of Red Cells, 1-32 (Blood Information Service); Schulman, Biochim. Biophys. Acta, 148:251-55 (1967); Leif and Vinograd, Biochemistry, 51:520-28 (1964). This is disputed, however, by Mortenson, Danish Med. Bull., 32:309,320 (December 1985).

A variety of biochemical changes are believed to be associated with erythrocyte senescence. Phytrakul, M.S. Thesis, Age-Related Changes in Red Cell Activities of Glycolytic Enzymes, Reduced Glutathione, and Hemoglobin Denaturation, 1-85 (University of Oregon Health Sciences Center, Portland, Ore.: 1976); Keitel, et al., Blood 10:370-76 (1955); Bernstein, J. Clin. Invest., 38:1572-86 (1959); Edwards and Rigas, J. Clin. Invest., 46:1579-88 (1967).

Polychronakos, et al., J. Clin. Endocrin. Metab., 55:290 (1982) discovered that most if not all of the difference in insulin binding seen between the RBCs of the adult and the newborn is attributable to a greater preponderance of younger RBCs in the latter. Earlier studies established that reticulocytes bound about twice as much insulin as the oldest cells.

Fitzgibbons, et al., J. Clin. Investig., 58:820-824 found that both normal and diabetic erythrocytes contained greater amounts of hemoglobin $HbA_{1a+b}$ and $Hb A_{1c}$ in the older cells. Likewise, Elseweidy, et al., J. Lab. Clin. Med., 102:628 (1981) felt that there is a red cell age-related increase in glyco Hb. On the other hand, Mortensen, Danish Med. Bull., 32:309, 320 (December 1985) reported that the differences in $HbA_{1c}$ content between "young" (slow-sedimenting) and "old" (fast-sedimenting) cells were not statistically significant.

There is evidence to the effect that during the lifespan of the RBC, HbA is slowly and irreversibly glycosylated. Maney, et al., Blood, 46:1051 (1975) (abstract); Ashby, et al., (1985), supra; but see Mortensen (1985), supra. If this occurs in a mathematically predictable manner, then the ratio of glyco HbA to HbA is indicative of the age of the RBCs and may be used to detect age-related changes in other metabolites.

Stillman, U.S. Pat. No. 3,864,571, describes a fluorescence-activated cell counter which will separately count lymphocytes, polymorphonuclear neutrophils, eosinophils, monocytes, basophils, platelets, and reticulocytes, based on differential staining of their nuclei and cytoplasm. Wheeless Jr., U.S. Pat. No. 3,497,690 distinguishes normal cells from carcinogenic cells by nucleic acid content, as determined by a fluorochrome dye. Kamentsky, U.S. Pat. No. 3,413,464 relates to methods of enhancing this distinction. Staining is also employed by Groner, U.S. Pat. No. 3,740,143. See also U.S. Pat. Nos. 2,875,666, Parker; Fulwyler, 3,893,767; Adams, 3,883,247; Kamentsky, 3,662,176; Elkin, 3,661,460; Ehrlich, 3,699,336; Tyrer, 4,172,227; Bouton, 3,873,974; Miller, 3,827,804; and Miller, 3,832,687.

Fulwyler, U.S. Pat. No. 4,499,052 distinguishes cells with different relative receptivities for two different labeling agents by the ratio of the two labeling agents bound to the cell (e.g., fluorescein and rhodamine labeled particles).

Rogers, U.S. Pat. No. 4,416,778 described a method of preparing neocyte-enriched blood for use in blood transfusions. Neocytes (young RBCs) were centrifugally separated from gerocytes (old RBCs) based on their difference in density.

SUMMARY OF THE INVENTION

A method for detecting and measuring a condition in a human or animal patient by time series analysis from a single sample of blood is described. A sample of blood is obtained from the patient, cells of the blood sample are stained for each constituent to be measured, the stained cells are measured quantitatively, on a cell-by-cell basis, and the measurements and/or calculated ratios are placed in order numerically. The numerically ordered cells are divided into a time series according to the length of life of the cell measured, thus obtaining a historical record of the condition.

It is an object of the invention to provide a time series analysis of a condition from a single sample of blood.

A further object of the invention is to compare the glycohemoglobin and hemoglobin contents of blood on a cell-by-cell basis.

Yet another object under the invention is to provide a method for obtaining a historical record of the past course of a physical condition.

DETAILED DESCRIPTION OF THE INVENTION

Red blood cells are released on a continuous basis into the blood stream and remain in circulation for 120 days under the influence of numerous normally present and abnormally present chemicals in the blood plasma. Some of these chemicals leave a record of their presence and concentration in the hemoglobin molecules of red blood cells. Since the record is cumulative and irreversible, appropriate measurement of such concentrations on a cell-by-cell basis permits the order of cells into a time series which becomes a historical record of the course of a physical condition. Among the many applications of this process are: control of sugar usage in diabetes, record of alcohol consumption or abuse, and record of compliance with therapeutic drug or other dietary regimens. The process can also be used to provide a record of abnormal destruction of red blood cells. Other purposes include: making or confirming a diagnosis of patient illness, monitoring progress of a patient illness or treatment, screening for common diseases, and establishing a patient baseline for future reference. Many important tests are normally repeated at intervals, thus establishing a time series on a patient which can be used to influence diagnostic and therapeutic judgments.

The present invention provides a time series result on the basis of a single sample being analyzed for historical data on a cell-by-cell basis. The time series result is provided in tabular and/or graphical format for blood constituents to be analyzed. Thus, the aging of red blood cells is studied in retrospect.

Knowledge of the relationship between hemoglobin, glucose, and red blood cell life span, has influenced the development of the process of the invention in which the average record of glucose concentration over the life span of the red blood cells is measured by analysis of the proportion of hemoglobin which has been reacted to form glycohemoglobin, to the total hemoglobin. This is performed as a chemical test by breaking down the red blood cells in a sample, separating the reacted hemoglobin from the unreacted hemoglobin, and measuring both of these constituents by the light absorbed by the pigment portion of the hemoglobin molecule. Measurement of hemoglobin and glycohemoglobin in cell lysates is known in the art.

Several such reactions, in addition to the reaction of glucose or other sugars with hemoglobin to form glycohemoglobins, are known. Thus, it can be predicted that a variety of drugs will have such reactions, either directly or indirectly. However, such reactions may be present in only small amounts and are therefore difficult to measure by the separation techniques currently in use. Such reactions will be considered below.

According to the present invention, the analysis of hemoglobin and of altered hemoglobin, for example, glycohemoglobin, is performed on a cell-by-cell basis. This is done by performing quantitative staining reactions for each constituent on cell suspensions or on cells plated on a glass slide, or by any other appropriate method. The cells are then measured optically for the stains, and several instruments exist for such measurement. Examples of such instruments are found in the patents to Fulwyler, U.S. Pat. Nos. 3,893,767, Stillman, 3,864,571, Elkind, 3,661,460, Groner, 3,740,143 and Kamentsky, 3,413,464. Patents for slide measurement instruments include those of Miller, U.S. Pat. Nos. 3,832,687 and 3,827,804. Bacus, U.S. Pat. No. 4,209,548 describes a pattern recognition instrument.

The results of the cell-by-cell measurements provide quantitative measures of an unaltered constituent of blood cells, such as hemoglobin, and an altered constituent, such as glycohemoglobin (also known as glycosylated hemoglobin). A ratio is taken, on a cell-by-cell basis of the altered constituent to the unaltered constituent (such as glycohemoglobin to hemoglobin), and the ratios are placed in numerical order. Since hemoglobin reacts with glucose, which circulates in the blood plasma, continuously and irreversibly, in older red blood cells this ratio is greater than in younger blood cells. Thus, the ordered set of ratios represents the relative ages of the cells from which the ratios have been derived. By placing these ratios into arrays of equal proportion, or equal concentration of the altered component, a true time series can be derived since it is known that the life of a red blood cell is 120 days.

When the alteration is constant and of some magnitude, such as in the case of the alteration of hemoglobin to glycohemoglobin, the time series may be chosen to have a resolution equivalent of two to seven days. When the alteration is small and less constant, the time series cannot be derived directly and reliably by the basic technique described above. By performing a combined analysis on the same cells, cell-by-cell, for hemoglobin, glycohemoglobin and other constituents to be analyzed, the time series derived for the glycohemoglobin can be used also to establish the time series for the other constituents to be measured. Thereby, a historical record of such other constituents may also be obtained. Any other modification process of a comparably reliable nature may be used to establish a reference timeline for comparison with more variable processes. Additionally, other methods of determining cell age, such as cell sedimentation rate, or the steady deterioration of unstable endogenous constituents of the red blood cells, may be used for calibrative purposes.

In addition to the ratio of glyco Hb to Hb, other determinants of cell age are considered by the invention. The steady, gradual deterioration of insulin binding and of glycolytic enzymes are amenable to staining and measurement.

The advantages of the present invention in the diagnosis and therapeutic monitoring of disease is clearly apparent. For example, in diabetes, where the patient has lost the usual control over metabolism of the sugar molecule (glucose) and therefore needs external modification of such control by administration of insulin, other medication, or by rigid control of diet, the day-to-day control of sugar can be examined in retrospect, for the previous 120 days, by analysis of a single blood sample. When this is done at three or four month intervals, a continuous record may be maintained, and such a record may be used to establish the day-to-day level of control. A batch test, done by previously known methods, only has the time resolution of 120 days at a single data point, in contrast to the process of invention in which the 120 day life span of red blood cells may be broken down into, for example, weekly intervals by time series analysis of a single sample, analyzed on a cell-by-cell basis, the single sample being taken at the end of the 120 day period. During the 120 days there may be some periods of high and other periods of low sugar concentration in the patient's blood plasma. Using previously known methods such separate episodes are averaged as one value, thus allowing errors to compensate for each other, possibly leading to a normal result on the batch test. Compensating errors are largely avoided by the methods of the invention as a historical time series divided into short time intervals is most likely to eliminate such errors.

While it is preferable that the reaction monitored to determine the age of the cell be totally irreversible, it is sufficient that the reaction be only slowly reversible. If it is slowly reversible, then the "history" preserved by oldest blood cells will be lost.

It is also preferable that the reaction be constant. However, if its rate changes in a consistent and predictable manner, then the age may be determined by the other means in order to calibrate the substrate:product ratio's relationship to cell age.

It is further desirable that the reaction occur throughout the life of the cell. However, if it occurs during a defined portion of the lifespan of the cell, then it can still be used to provide time series data, albeit over a more limited period.

Non-toxic analogs to the sugar molecule can also be used as independent labels. Such independent labels can be mixed with medication by pharmaceutical companies, the mixture being of constant proportion of label to medication. The label is preferably a substance which reacts with a cell constituent, such as hemoglobin, irreversibly and at a constant rate. By such means a historical record of consumption of any drug may be provided. A record of this nature may be utilized in determining compliance to a drug therapy regimen, and may be useful as a record of accidental or unprescribed ingestion of the medication.

Preferably, the labels used are rare sugars not found in the normal diet, such as rhamnose and xylose. Cook and Menzies, Digestion, 33:109-116 (1986) used "non-metabolized" markers to assess intestinal absorption. See also Ford, et al., J. Ped. Gastroent. & Nutr., 4:568-74 (1985).

In a non-diabetic patient, the same glycohemoglobin analysis performed on a cell-by-cell basis can also provide a historical record of the life span of the red blood cells in circulation at the time the sample was taken. For example, if the maximum concentration in a single cell is only 1/10 of that found in a normal sample, then the life span of red blood cells in this patient is only 12 days instead of 120 days. The method of the invention provides means of improving diagnostic accuracy for diseases of red blood cell destruction, as compared to diseases of blood loss from bleeding. Evaluation of RBC destruction in a diabetic patient is also possible.

To use the process of the invention, a fluid sample is taken from a person (or animal) and is treated in one of two general ways:

(1) The fluid sample of blood is plated onto a flat surface, for example, a glass slide. This can be done by a conventional manual technique, or by a blood spinner technique as described in U.S. Pat. No. 4,209,548. The plated sample may either be fixed while still wet as described in U.S. Pat. Nos. 4,209,548 and 4,483,882, or the plated sample may be permitted to dry on the slide and then is fixed by conventional methanol immersion, or other conventional techniques.

(2) An alternative method of treating the sample is to retain it in fluid form and permit the red blood cells to settle away from the plasma. Centrifugation may be used to speed up this settling process. The upper, plasma layer is removed and replaced with a buffer solution having properties selected to preserve the form of the red blood cells. Settling (and centrifugation) are repeated, and a second volume of buffer is applied, thus washing the cells. After washing, the cells may again be treated in one of two ways, either plated on a flat surface as generally described in (1) above or they may be retained in suspension during the staining step.

If the cells are retained in suspension for the staining step, the cells must be fixed to preserve their shape and to permit the penetration of dyes and other reagents. Such fixation may be accomplished by use of dilute solutions, for example, ethanol in buffer, or formaldehyde in buffer. After fixation, the cells are again washed to eliminate the influence of the fixative reagent. However, in the case of aldehyde fixatives, further addition of a reagent such as dimedon may accomplish the same end as washing, by neutralizing the fixative.

The samples which have been plated on flat surface may be washed similarly, except that this is accomplished by dipping the flat surface into a clean solution. One purpose of washing is to eliminate extraneous sugar molecules, or other label, as yet unattached, from the red blood cells.

After washing and fixation, either in suspension or on a flat surface, the red blood cells are next stained so that one or more characteristics may be measured. Since the hemoglobin molecule is a pigment and has characteristic light absorption properties when fixed, it may not be necessary to perform further identification of this molecule. However, it is also possible to stain the hemoglobin by conventional protein stains, such as fluorescein isothiocyanate. A number of reagents of different fluorescent colors and of different excitation wavelengths are readily available for this purpose. Although hemoglobin is not the only protein present in red blood cells, it is in excess over other proteins in such large proportions that the accounting of their quantity does not influence the result.

In addition to staining for hemoglobin, the sample is also stained for another constituent, for example, glycohemoglobin (glucose attached to the hemoglobin molecule). Other labels may also be applied, as discussed above, and as described in the specific examples below. After each staining step, it may be necessary to perform washing steps to eliminate the effect of reagents on subsequent steps of the procedure.

After completion of staining, the sample is measured by a cell-by-cell method. Apparatus for such measurement is described, for example in U.S. Pat. Nos. 3,413,464 and 3,893,767. The exact nature of the color filters used for the measurement depend on the exact implementation of staining of the sample.

The glycohemoglobins may be detected in several ways. Enzymes may be used which act upon the carbohydrate moieties to release active species which participate in a signal generating system. Labelled lectins or carbohydrate specific antibodies may be bound to the glycohemoglobin and the resulting complex then detected.

Each cell is measured for at least two components and the resulting data from such measurements are retained in the instrument memory for further analysis until the final results are reported. The process readily lends itself to analysis by computer methods. Calculations include obtaining the ratio of the at least two components which have been measured, still on a cell-by-cell basis. The ratio results are placed in ascending order and are plotted in histogram or other fashion for graphical presentation. The quantitative measurement of the at least two components, on a cell-by-cell basis, may take place either concurrently or consecutively on the same cell.

The same data of ordered ratios is also used in the following computation. Starting at one end of the order, a constant fraction of the total number of cells counted is counted off and their ratio is averaged, the average being recorded either manually or in a computer memory. Similar constant fractions are counted off repeatedly and their ratios averaged and stored until the other end of the order is reached. The number of such constant fractions represents a fractional increment of time of the total life of the individual red blood cells. The exact nature of this increment of time will depend on further knowledge of the individual from whom the sample is taken. As an example, a sample from a normal human with red blood cell life span of 120 days, whose ordered sample has been divided into 60 constant fractions, will have each fraction representing two days. It is to be understood that some imprecision will exist in such representation, depending on the biological variation, for example, of the number of red blood cells produced on each day of the previous 120 days. Therefore, larger fractions representing longer time intervals will generally have improved precision, at the expense of resolution.

As secondary test of the validity of constant fractions representing constant time intervals, the instrument may perform a standard deviation, and/or other simple statistical calculations, on each set of ratios within a constant fraction. Starting with a fraction close to the middle, the fraction is enlarged and diminished in a systematic way and a standard deviation again calculated. By rapid iterations of this technique, the best fit for each interval is thus defined, and the average for the new interval is calculated and used to replace the original stored values for the interval. The difference between each average and the next previous average in the order is calculated. This calculation represents the increment of label aggregated into the red blood cells during the time intervals represented by the average.

In this manner, both the relative ages of each measured red blood cell and the amount of aggregated label in each time interval are defined. For different types of sample, it may be necessary to make further adjustments to the calculation. Such adjustments may improve the means of defining time intervals when the history of cell survival is better known. For example, if red blood cells generally live for 120 days, but an episode of red blood cell loss happens at known intervals, as in human females in their menstrual cycle, then an appropriate correction factor will be applied.

Similarly, care should be taken if the patient is known to have received a blood transfusion, since glycohemoglobin levels in the transfused cells may reflect, in part at least, the glucose levels in the donor rather than in the patient.

In addition to the two measurements already described, further measurements also may be made. One purpose for making further measurements on each cell is to determine yet another label which is aggregating at the same time in the individual from whom the sample is taken.

Another purpose for making further measurements on each cell is to achieve a better definition of the time interval to be studied. For example, by measuring the amount of ribonucleic acid (RNA) in each cell, as described in U.S. Pat. No. 3,864,571, the most recent two days of red blood cell life may be studied, since RNA is only present in a red blood cell for the first two days of the life of the cell. By limiting the measurement of label and label ratio, etc. to only these one-day old and two-day old cells (known as reticulocytes), the immediate past history of label processing in the individual is determined. Thus, if the cells have been stained and are measured for hemoglobin and glycohemoglobin, and if RNA is also measured, the measurements all being made on a cell-by-cell basis, glucose control for each of the two days previous to the day the sample was taken may be studied. If a further label is also measured on these cells, on a cell-by-cell basis, at the same time, for example, alcohol or a particular drug may be labeled and measured, the ingestion of the alcohol or drug during each of the previous two days may be studied since the relevant cells for these days have been identified by the additional presence of RNA in these cells.

Figure 1A:
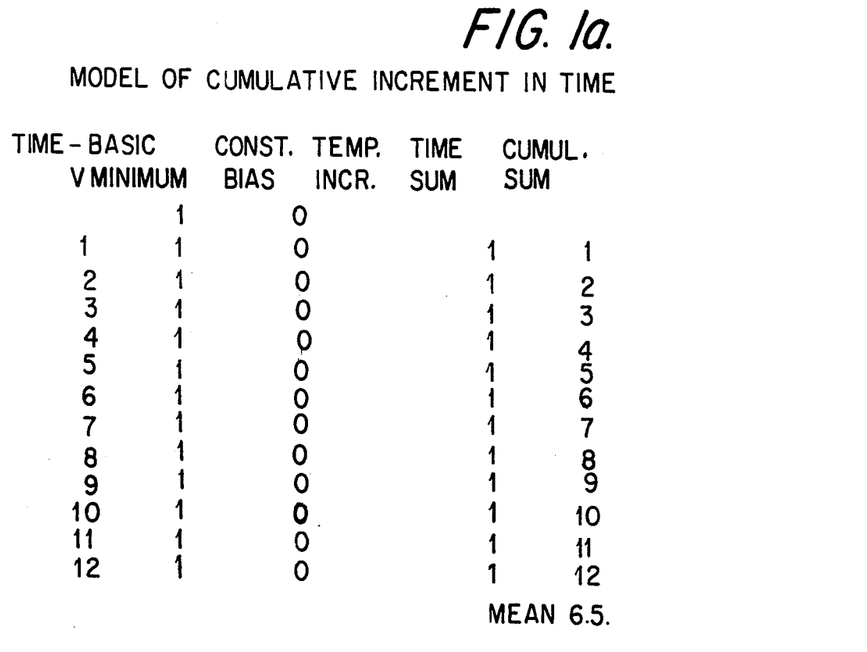
FIGS. 1a and 1b show patient chemistry in a normal patient.

A simple model showing the use of the invention is illustrated below. FIG. 1a shows a composite of an incremental table showing the numbers and rules of the model. Column 1 represents increments in time, for example, weeks; Column 2 represents a base line addition for each time interval, the base line being representative of the rate modifying red blood cells in circulation in a normal individual; Column 3 represents a constant abnormal increment related to the patient's disease process (in FIG. 1, this is zero for a normal patient); Column 4 represents non-constant increments related to temporary changes in the patient's chemical status within one time interval only (zero in a normal patient); Column 5 represents the sum within one time interval of Columns 2, 3 and 4; Column 6 represents a cumulative number based on all the time intervals from the first interval or row to the current interval or row. At the bottom of column 6, the average increment, or mean, is represented. This mean is derived by dividing the cumulative total of column 6 by the number of time increments. The numbers in the model of FIG. 1a are devised in such manner that the average increment simulates the normal total glycohemoglobin value when only baseline values take part in the cumulation.

Figure 1B:
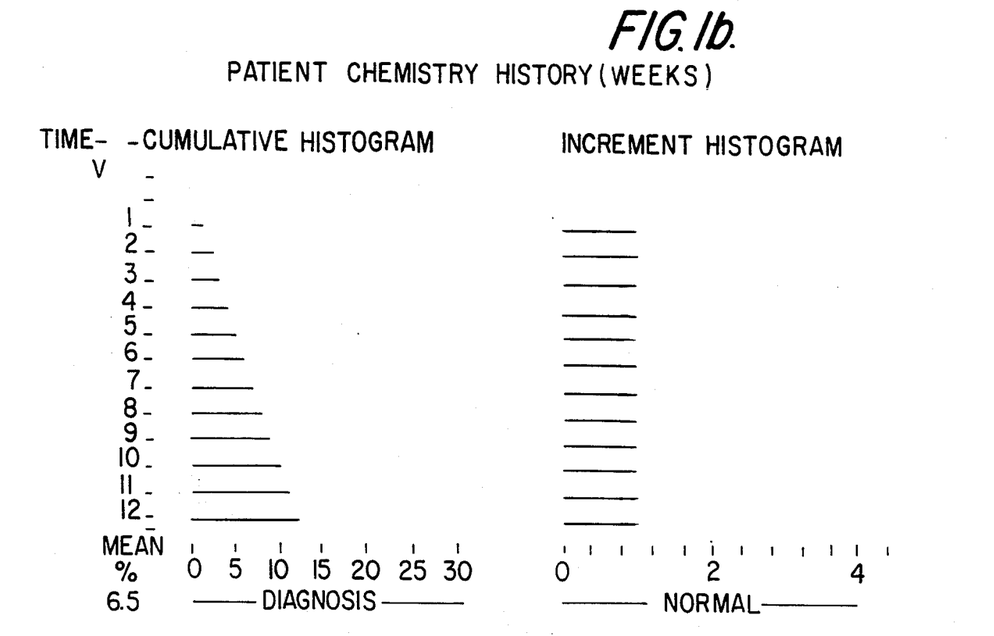

FIG. 1b illustrates a cumulative distribution curve based on Column 6 of FIG. 1a. FIG. 1a illustrates how the altered hemoglobin molecule accumulates with time in red blood cells of different ages as represented in Column 1.

The third component of FIG. 1 graphically represents the incremental modification of hemoglobin in each single time interval. This is the graph which would be of most interest to a physician in the treatment of patients with, for example, diabetes. This also represents the quantity of the modifying substance circulating in the plasma at the time interval represented for the single time interval.

Figure 2A:
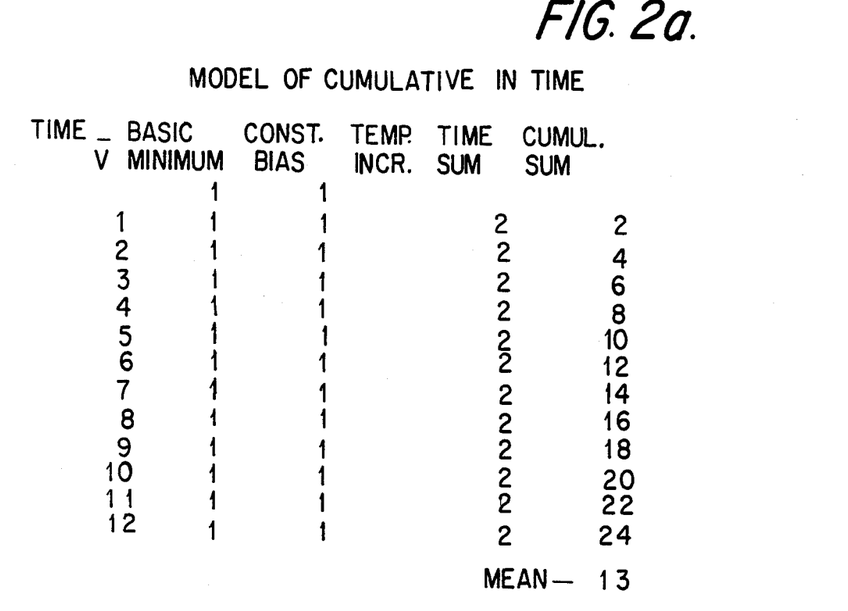
FIGS. 2a and 2b shows patient chemistry in an out-of-control diabetic.
Figure 2B:
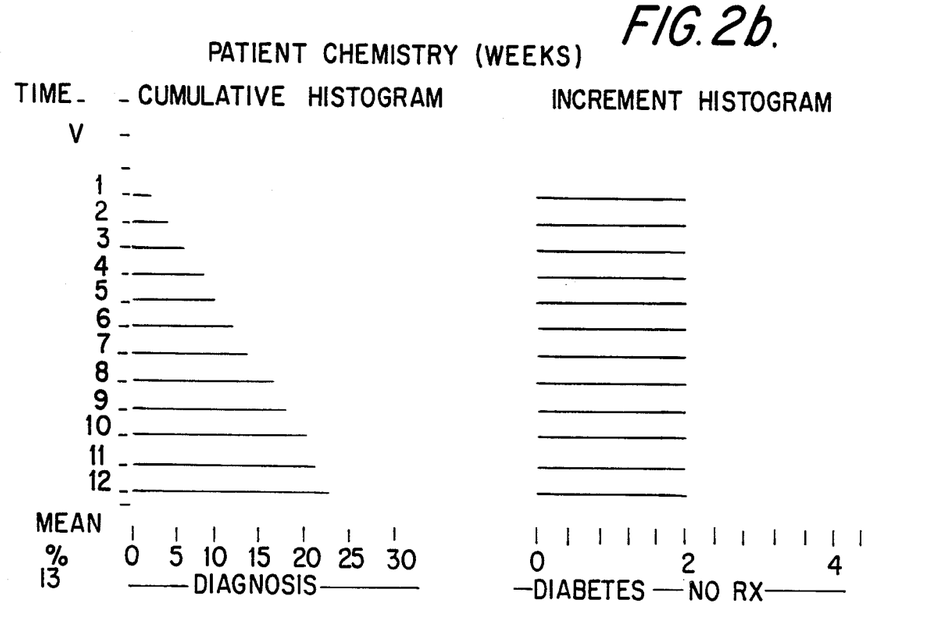

FIGS. 2 through 5 are similar to FIG. 1, described above. In FIG. 2, the values simulate a severe diabetic whose sugar concentration is always out of control by a constant increment equal to the baseline increment, that is, the circulating sugar value is always twice normal. The values in FIG. 2a are graphically represented in FIG. 2b which shows the degree of loss of control of sugar concentration.

Similarly, drug usage may be monitored. Thus, morphine addiction is associated with increased glycohemoglobin levels. Giugliane, Diabetologia, 22:379 (982).

Figure 3A:
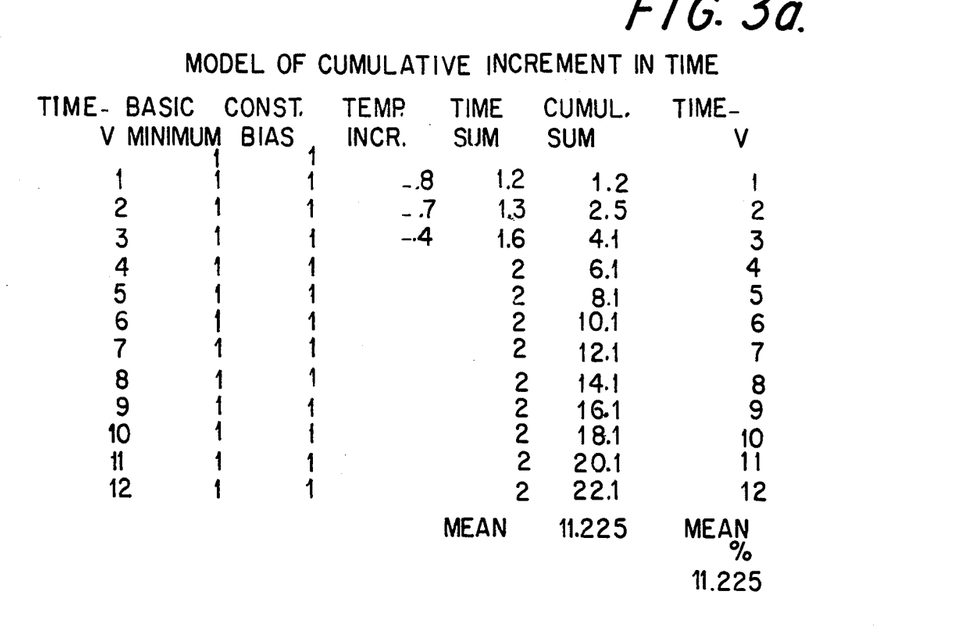
FIGS. 3, 4, and 5 show patient chemistry for the patient of FIG. 2 at different stages of treatment.
Figure 3B:
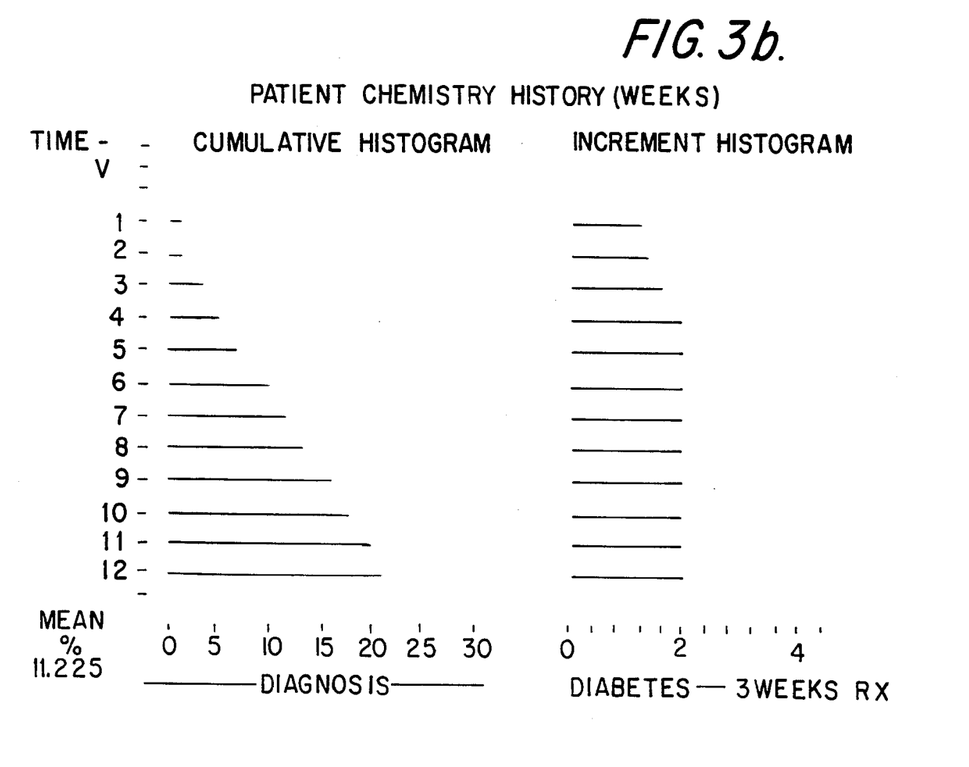
Figure 4A:
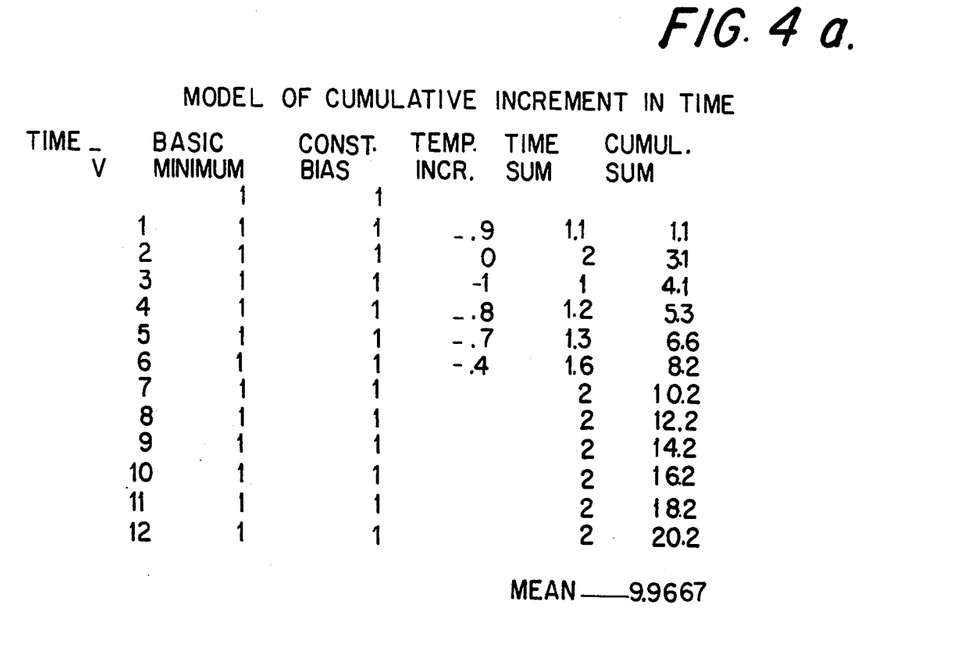
Figure 4B:
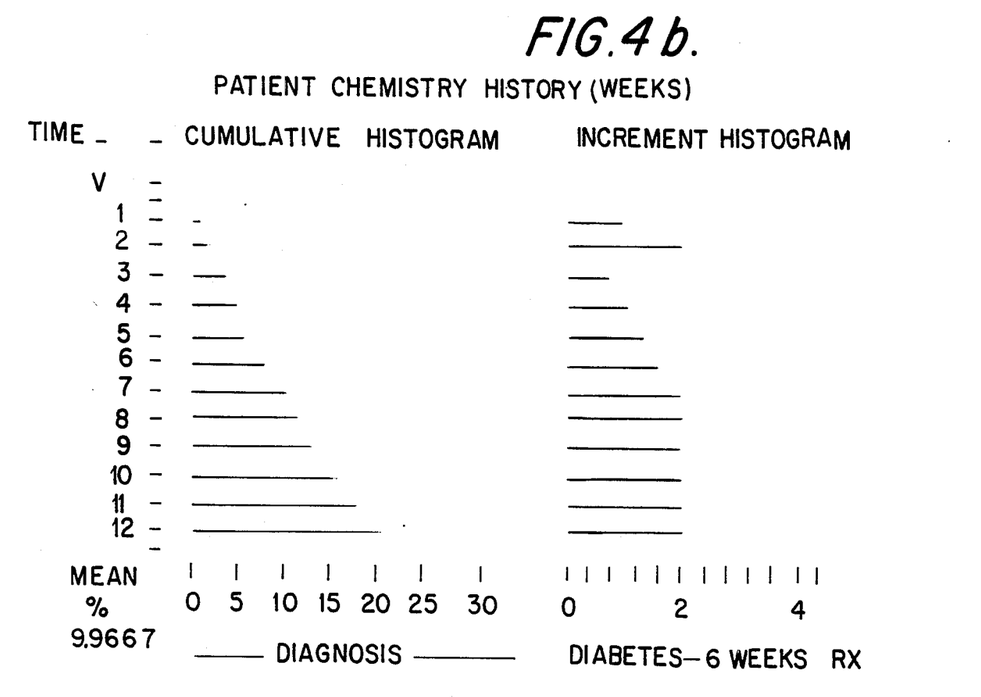
Figure 5A:
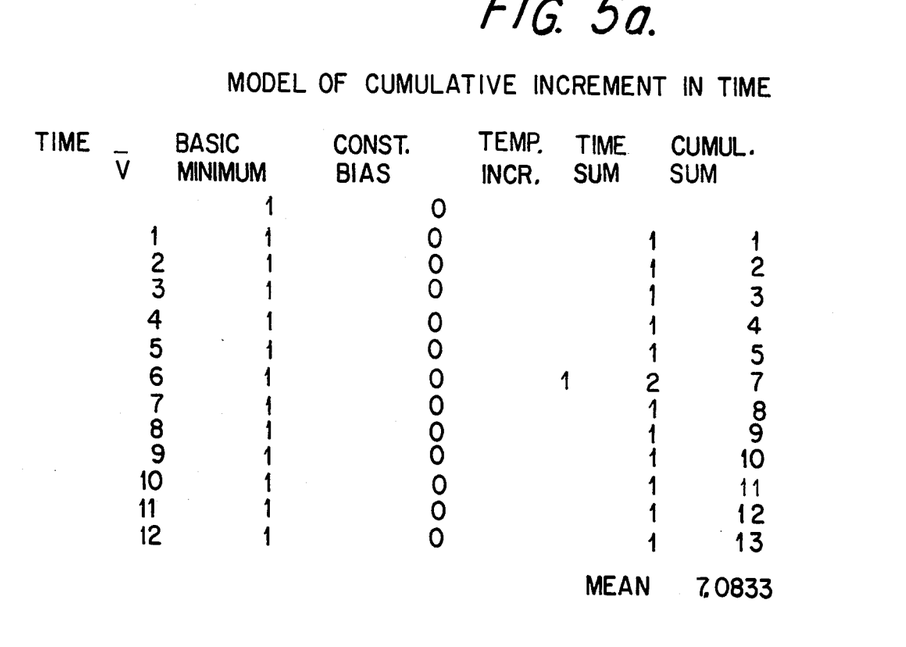
Figure 5B:
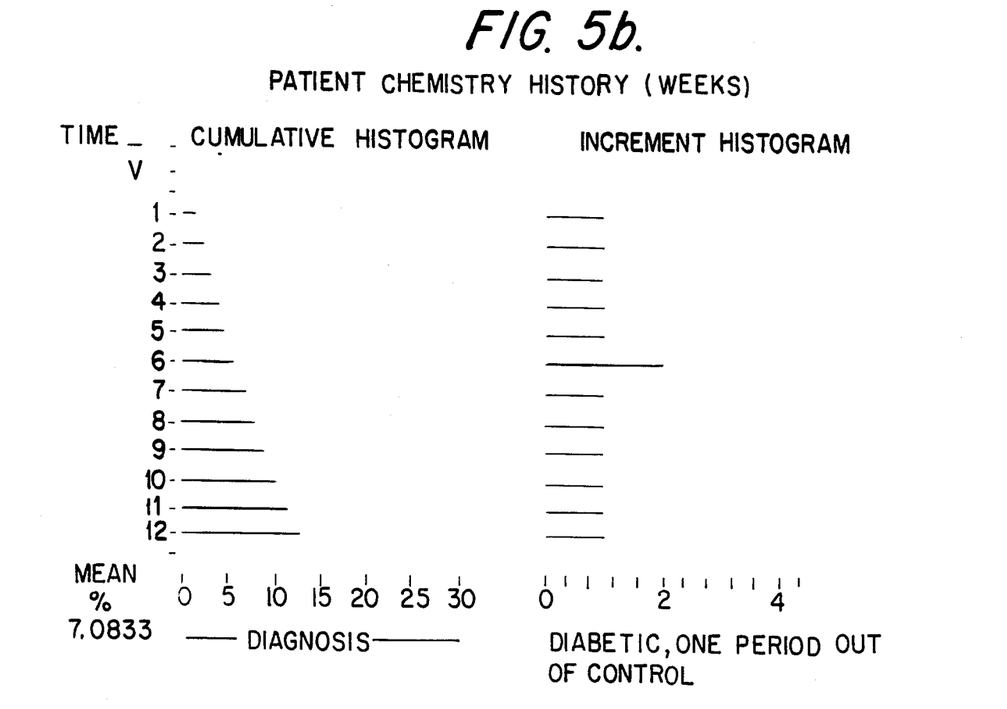

FIG. 3 shows results of therapeutic treatment on the hypothetical patient of FIG. 2, for the first of three time intervals (shown in FIGS. 3, 4, and 5). This is represented by a negative increment due to the effects of medication, for example, insulin. The effect of this therapy is graphically represented in FIG. 3b. In FIGS. 4 and 5, further periods of insulin therapy of the same patient are modeled, and illustrated graphically in FIGS. 4b and 5b. The success of the therapy is shown as the incremental graph returns toward the normal shown in FIG. 1. Absence of complete return of this patient to normal values is shown in the aberration of the incremental curve in FIG. 5.

The invention is further illustrated by the following non-limiting examples:

EXAMPLE 1

A liquid blood sample is taken from a diabetic man known to be free of significant blood loss during the previous 120 days. A portion of the sample is washed with phosphate buffered saline (PBS) at pH 7.4 and is applied to a microscope slide by a spinner process. The sample is air-dried, fixed by immersion in dry methanol for 30 seconds, and air-dried again.

The air-dried sample is immersed in distilled water for two minutes, and then immersed in a solution of 0.5% periodic acid for 20 minutes. Then the same sample is immersed in running water for 10 minutes, and placed in a Schiff solution for another 20 minutes. The Schiff solution is composed of 0.5 gm of yellow-fluorescing (540 nm) acriflavine hydrochloride, 20 ml. of 1N hydrochloric acid, and 1 g of sodium metabisulfite in 200 ml of distilled water. This solution is permitted to age for 1 day, after which it is filtered together with activated charcoal, and the clear amber filtrate is stored at 4° C. A final rinse in tap water eliminates excess reagent.

The obtained sample is stained in red-fluorescing (620 nm) Bromophenol Blue 0.2 gm % in methanol, washed three times in methanol and air-dried. After thorough drying the sample is covered with a cover glass, using a mounting medium which is free of fluorescence.

Individual cell-by-cell measurements are made on a fluorescence microscope similar to that described by Fulwyler, U.S. Pat. No. 3,893,767. Ten thousand red blood cells are measured and incorporated in a database for analysis. Ratios of yellow to red fluorescence are measured and the results ordered by magnitude from the smallest to the largest ratio. The ordered cells are put into groups of about 600 cells starting at the lowest ratio and the results are averaged. Each average is subtracted from the next higher average and the remainders are plotted graphically in a histogram representing a weekly history of the patient's control of blood sugar. Results are compared by a physician with knowledge of normal variations.

EXAMPLE 2

A liquid sample of blood is taken from a known female diabetic in an emergency ward, where she arrived unconscious. The blood sample is washed twice with PBS, and then 100 microliters containing about 2 million cells of the sample are mixed with a 0.5% solution of formaldehyde in PBS. After 5 minutes the cells are again washed twice with clean portions of PBS. The washed cells are mixed with a solution of TRITC labeled Concannavilin A (Con A). The Con A has the characteristic of being able to attach to glucose molecules which are themselves attached to the hemoglobin molecule. This solution is made up in PBS and 0.1% nonanionic detergent solution (Tween 20). After allowing this solution to act on the cells for 20 minutes, the cells are again washed, and the suspension is made up to a final concentration of ½ million cells per cubic centimeter. This final suspension of cells is permitted to flow through a flow cytometer such as the Becton Dickinson FACS Analyzer, using excitation filters limiting wavelength to 545 ±20 nanometers. Fluorescence filters are used such that two colors of fluorescence are measured, one above 620 nanometers and one below 580 nanometers. Cross interference between the two fluorescent colors is determined experimentally and corrected. Twenty-four thousand cells are measured and the data accumulated in "list mode" in the instrument's computer memory.

Ratios are calculated as in Example 1 and the results are distributed into two day intervals. Standard deviations are used in the computer to test the averages in an iterative way until best fit of data is achieved for each interval. The daily increments of aggregation are calculated as in Example 1, and the results reported on this patient's Glucose Control History.

EXAMPLE 3

The procedure of Example 2 is followed, except that before the washed cell suspension is treated with formaldehyde solution, it is mixed with a solution of 0.4% new methylene blue (NMB) and 1% potassium oxalate. After 4 minutes, an equal volume of the formaldehyde solution is added, and after a further two minutes, the suspension is washed as in Example 2. All other staining steps are as in Example 2, but all steps, including the first wash step, contain 0.2% cetyl pyridinium chloride (CPC).

Measurement also is as in Example 2, but in addition, the wide angle light scattering of each cell is measured and recorded, together with the other two measurements in list mode. The NMB will have caused aggregation or precipitation of RNA in reticulocytes. The precipitates inside the cells are maintained as solid masses with higher refractive index by addition of CPC to all solutions. Since CPC is nonfluorescent it will not interfere with the other measurements. It will, however, cause significant increase of light scatter in reticulocytes.

Data analysis proceeds as in Example 2. A separate data analysis is made of those cells which have large light scattering results. These cells are divided into two equal numerical groups. Those with the largest amount of light scattering represent the day before sample was taken. Those with less light scattering represent the day previous to that. In this way the history of glucose control for the two days prior to the emergency can be specifically determined.

EXAMPLE 4

The procedure used is as in Example 3, but the prepared sample is placed on a glass slide and measured under a microscope using three colors of analysis.

EXAMPLE 5

Red blood cells are prepared by washing in phosphate buffered saline (PBS) as in example 1. The red blood cells are plated onto slides as in example 1. Two slides are prepared and receive separate staining procedures.

Slide A is stained as in example 1.

In Slide B the periodic acid step of example 1 is replaced by immersing the slide in a solution containing 3 units per ml of galactose oxidase, an enzyme isolated from the organism *Polyporus circinatus* or *Dactillium dendroides* which is available from Sigma Chemical Company. The said solution also contains a nonionin Sigma detergent, 0.1% Tween 20, and 10 units per ml of catalase and dilute buffer adjusted to pH 6.0. Galactose oxidase has the property of oxidizing the sugar galactose or end group galactose in polymeric sugars to a compound having a dialdehyde similar to that produced by periodic acid, however, the enzyme is specific for galactose and several related sugars such as galactosamine, raffinose and stachyose; it will not react with glucose. Catalase is included to use up the excess hydrogen peroxide developed in the reaction and diffusing away from the cells.

After treatment with the galactose oxidase solution and washing in distilled water, Slide B is treated with Acriflavine Schiff solution as in example 1 and also with bromphenol Blue, as in example 1.

Quantitative cell by cell determination of the two fluorescent colors as in example 1 enables calculation of the ratios and development of the calendar with slide A.

In a normal person slide B will fail to show increments from which a calendar could be computed. However in a patient suffering from galactosemia the result will be a calendarisation with increments dependent on the quantity of galactose ingested by the patient.

Therefor the test whereby periodic acid is replaced by galactose oxidase makes the reaction specific for hemoglobin altered by galactose. Such a test may be used in monitoring diet of a patient with galactosemia, and may also be used in estimating the interference of galactose in the glucose increments.

See Bradley A. Schulte and Samuel S. Spicer, "Light Microscopic Histochemical Detection of Terminal Galactose or N-acetyl Galactosamine in Rodent Complex Carbohydrates, Using a Galactose Oxidase-Schiff Sequence." J. Histochemistry and Cytochemistry, vol. 31, page 19–24, 1983 ; N. J. Howard, H. Monaghan and J. M. Martin "Hemoglobin A1 in Galactosemia, a Possible Role in Monitoring Dietary Compliance." Acta Paediatr. Scad, Volume 70, page 695–698, 1981.

EXAMPLE 6

Sample of whole blood is washed, plated on slides and fixed as in example 1.

The slide is then treated with a solution of 0.1% Tween 20, 3 units per ml of galactose oxidase, 5 units per ml of horseradish peroxidase, and 2 mg per ml of a reagent 4-chloro-1-naphthol for 10 minutes. The resultant red blood cells will take on a dark blue-black coloration quantitatively dependent on the amount of galactose-modified hemoglobin present in the cell.

Measurement in this case is made by light absorption at 410 nanometers, for the hemoglobin component, and at 600 nanometers for the reaction product dependent on the presence of galactose. However the resultant quantitation and calendarisation is performed as in the previous examples and the interpretation of this example is similar to example 5. It is generally not possible to do light absorption for the detection of the hemoglobin pigment after periodic acid reactions as in the previous examples because the periodic acid destroys the pigment nature of the hemoglobin. However in this example periodic acid is replaced with an enzyme reaction, which does not destroy the hemoglobin pigment. Therefore the pigment is available for direct measurement.

EXAMPLE 7

Sample of whole blood is washed, plated and fixed on slides as in example 1.

The slides are treated in a solution containing 0.1% Tween 20, and 0.1 mg/ml of the peroxidase derivative of the lectin, *Maclura pominifera* agglutinin (MPA), which specifically binds to alpha-D-galactosyl derivatives. Following a brief distilled water wash, the slide is next treated with a solution of 0.03% hydrogen peroxide and 0.2mg/ml of 4-chloro-1-naphthol. Following a brief distilled water wash, the slide is further treated with a solution of 0.5% hydrogen peroxide to inactivate the peroxidase enzyme used in this part of the sequence.

Following another brief wash in distilled water, the slide is further treated with the peroxidase derivative of the lectin, *Pisum sativum* agglutinin (PEA), which binds specifically to derivatives of glucose and of mannose. After a further brief distilled water wash, the slide is treated with 0.03% hydrogen peroxide and 0.2 mg/ml of 3-amino-9-ethyl-carbazole, a chromogen producing a red reaction product in the presence of hydrogen peroxide and the enzyme peroxidase. A final distilled water wash is performed and the slide is mounted under a cover glass for measurement.

The slide treated with lectins as above is subjected to cell-by-cell measurement at three wavelengths of light; 410 nm, for measurement of total hemoglobin, 600 nm for measurement of reaction products of 4-chloro-1-naphthol which represents the amount of galactose modified hemoglobin, and 550 nm for measurement of the reaction product of 3-amino-9-ethylcarbozole which represents the amount of glucose-modified hemoglobin.

The cell measurement results are formulated into ratios of glucose modified hemoglobin to total hemoglobin, and of galactose modified hemoglobin to total hemoglobin. These two ratios for each cell are kept in joint lists so that the cells once ordered and calendarized for the glucose modified hemoglobin ratio will also have calendarized the cells for the galactose modified ratio. This combination of ratios is useful when the second alteration to hemoglobin, in this case galactose is present in such small amounts that it would be difficult to form a calendar from it independently.

The lectins and other reagents used in this example are available from various sources, for example from Polysciences, Inc., 400 Valley Road, Warrington, Pa. 18976.

EXAMPLE 8

Differences in insulin binding between neocytes and gerocytes may be used to determine the age of a blood cell on a cell-by-cell basis. A blood sample is incubated with insulin, washed, and incubated with an insulin binding protein (e.g., an antibody) labeled in some manner, such as with fluorescein. The sample is washed, fixed with dilute formalin or paraformaldehyde, and washed again. The sample is incubated with a rhodamine conjugate of the lectin from Streptomyces 2755 in 0.2% Tween 20. This lectin has an unusually great affinity for L-Rhamnose. If L-Rhamnose was supplied in a capsule or tablet in fixed proportion to a drug, it will be bound by the lectin. Cells exposed to high levels of the drug will incorporate correspondingly higher amounts of rhamnose and thereby bind more of the labeled lectin. The age of the cells is determined by measuring the intensity of the label on the anti-insulin antibody and comparing it with the intensity of fluorescence of the rhodaminelectin conjugate.

While the invention has been described above with respect to certain embodiments thereof, it will be appreciated that various changes and modifications may be made without departing from the spirit and scope of the invention.

I claim:

1. A method of discerning a condition of the body which is indicated by a change in the relative preponderance of red blood cells of different ages, which comprises: (a) providing red blood cells from a patient; (b) measuring, on a cell-by-cell basis, the level of a substrate constituent and the level of a product constituent of said cell; (c) determining, on a cell-by-cell basis, the ratio of the measured levels of said constituents, wherein said substrate constituent and said product constituent are related in that the substrate constituent is essentially irreversibly converted into the product constituent over a selected portion of the lifespan of the blood cell; (d) comparing said ratio to the reference ratios determined for red blood cells of known ages to obtain the actual age distribution of the cells, and (e) comparing that distribution to a reference distribution.

2. A method for ascertaining a condition in a patient which comprises (a) providing red blood cells; (b) determining the age of the cells on a cell-by-cell basis; (c) measuring the level of an indicator constituent in each of said cells; and (d) determining the dependency of the measured level of the indicator constituent on the age of the red blood cell for said cells, wherein said indicator constituent is characterized as a constituent whose level in a red blood cell is dependent on the age of the cell and said dependency is altered when said condition is present.

3. A method of determining the historical levels of a substance in the bloodstream over a particular period from a single red blood sample, which comprises (a) providing a sample of red blood cells; (b) determining the age of the red blood cells on a cell-by-cell basis; (c) measuring the level of an indicator constituent in each cell; (d) and comparing the level of said indicator constituent of the red blood cells with the age of the red blood cells on a cell-by-cell basis, said period not exceeding the lifespan of the red blood cells, wherein said indicator constituent is characterized as a red blood cell constituent whose level in the cell is quantitatively affected by the level of said substance in the bloodstream.

4. A method of obtaining a continuous record of a condition in a patient from samples of red blood cells taken at longer than monthly intervals which comprises (a) providing samples of red blood cells at least as frequently as every four months; (b) determining the age of each red blood cell; (c) measuring the level of an indicator constituent in each cell; and; (d) on a cell-by-cell basis, comparing the age of the red blood cells with the level of an indicator constituent of the cells which is indicative of the condition of the patient at a particular stage in the past life of the cell, said indicator constituent being characterized as a red blood cell constituent whose level in the cell is responsive to said condition.

5. A method of ascertaining whether a patient has been complying with a dietary or therapeutic regimen which comprises (a) providing a sample of red blood cells; (b) determining the age of each red blood cell; (c) measuring the level of an indicator constituent in each cell; and (d) on a cell-by-cell basis, comparing the level of an indicator constituent with the age of the cell, said indicator constituent being characterized as a red blood cell constituent whose level in the cell is responsive to said regimen.

6. The method of claims 2, 3, 4 or 5 where the age of the cell is determined by (i) measuring the level of a substrate constituent and the level of a product constituent on a cell-by-cell basis; (ii) calculating the ratio of said measured levels of a cell-by-cell basis wherein the substrate constituent is essentially irreversibly converted into the product constituent by the cell over a selected portion of the lifespan of the cell, and (iii) comparing said ratio to the ratio obtained in cells of a known age.

7. A method of determining the ages of the red blood cells in a sample on a cell-by-cell basis which comprises (a) providing a sample of red blood cells; (b) measuring the level of a substrate constituent and the level of a product constituent of said cells on a cell-by-cell basis and calculating the ratio of said levels on a cell-by-cell basis, wherein the substrate constituent is essentially irreversibly converted into the product constituent by the cell over a selected portion of the lifespan of the red blood cell; and (c) comparing said ratio in said cells of unknown age to the ratio obtained in red blood cells of a known age falling within said selected portion, so as to determine the age of the cells on a cell-by-cell basis.

8. The method of claim 7 wherein prior to step (b) at least one of said constituents is labeled with a fluorescent label, each such label having a distinctive wavelength of fluorescence, and the level of said labeled constituent is measured by measuring the intensity of fluorescence of the cell at said wavelength.

9. The method of claim 8 wherein one label is tetramethyl rhodamine isothiocyanate.

10. The method of claim 7 wherein at least one constituent includes a carbohydrate moiety and the constituent is labeled prior to step (b) with a label conjugated to a substance having an affinity for carbohydrate, and the level of said labeled constituent is measured by detecting and quantifying said label in said cell.

11. The method of claim 10 in which the carbohydrate-binding substance is Concanavalin A.

12. A method of determining the relationship of the level of an indicator constituent in a red blood cell to the age of the red blood cell which comprises, on a cell-by-cell basis, comparing the level of the indicator constituent and the age of the red blood cell, where the age is determined by the method of claim 9.

13. The method of claim 9 in which reticulocytes are distinguished from non-reticulocytes.

14. The method of claims 2 or 3 in which the condition is the level of a therapeutic agent in the blood, and the indicator constituent is that therapeutic agent or a cellular metabolite of that therapeutic agent found in erythrocytes.

15. The method of claims 2 or 3 in which the condition is the blood sugar level and the indicator constituent is a blood sugar.

16. The method of claim 2 or 3 in which the condition is the level of alcohol in the blood and the indicator constituent is alcohol or a cellular metabolite of alcohol found in erythrocytes.

17. The method of claim 5 which further comprises administering to the patient a pharmaceutical composition including a drug called for by said therapeutic regimen in fixed proportion to a nontoxic indicator, said indicator becoming or modifying a red blood cell constituent to provide the indicator constituent.

18. The method of claim 13 in which one-day old reticulocytes are distinguished from two-day old reticulocytes.

19. The method of claim 11 in which the product constituent is a glycohemoglobin and is labeled with a fluorochrome/lectin conjugate.

20. The method of claim 19 in which the lectin is Con A.

21. The method of claim 13 in which reticulocytes are identified by their RNA content.

22. The method of claim 21 in which the cells are treated with an RNA precipitating means.

23. The method of claim 21 in which the precipitating means is new methylene blue.

24. The method of claim 22 in which the RNA precipitates are distinguished on the basis of their refractive index.

25. The method of claim 24, in which the cells are also treated with cetyl pyridinium chloride.

26. The method of claim 2 in which only a defined subpopulation of blood cells is provided for age analysis.

27. The method of claim 12 wherein the comparison step further comprises measuring the two constituents on a cell-by-cell basis and deriving a ratio of the two constituents for each cell, ordering the ratios in numerical order to obtain an ordered list, and subdividing the ordered list into subdivisions corresponding with particular age brackets.

28. The method of claim 27 in which the subdivisions are adjusted to correct for expected episodes of blood cell loss.

29. The method of claim 1, 2 or 3 in which the cells are red blood cells.

30. The method of claim 6 in which the substrate constituent is a hemoglobin.

31. The method of claim 30 in which the product constituent is a glycohemoglobin.

32. The method of claim 31 in which the product is a glucohemoglobin, and is detected by a label having an affinity for glucose.

33. The method of claim 31 in which the product is a galactohemoglobin, and is detected by a label having an affinity for galactose.

34. The method of claim 17 in which the indicator is a sugar.

35. The method of claim 34 in which the sugar is essentially not a part of the normal diet.

36. The method of claim 10 where the carbohydrate moiety is L-Rhamnose and the substance is the rhamnose-binding lectin of streptomyces 2755.

37. The method of claims 2, 3, 4 or 5 where the age of each cell is determined from the insulin-binding capacity of the cell.

38. The method of claim 6 in which the conversion occurs at an essentially constant rate.

39. The method of claim 33 in which the product constituent is measured by treating the product constituent with galactose oxidase and measuring the level of the aldehyde produced by the action of galactose oxidase upon the galactohemoglobin.

40. The method of claim 32 in which the product constituent is measured by binding of the galactose moiety of the product with a labeled *Pisum sativum* agglutinin to obtain a labeled conjugate of the product constituent and the labeled agglutinin, and quantifying the labeled conjugate thus obtained.

41. The method of claim 31 in which the product is measured by reacting the product with periodic acid to obtain an aldehyde and quantifying the resulting aldehyde.

42. The method of claim 2, 3, 4 or 5 where the age of each cell is determined from the glycolytic enzyme activity of each cell.

* * * * *